United States Patent [19]
Clarke

[11] Patent Number: 5,139,334
[45] Date of Patent: Aug. 18, 1992

[54] HYDROCARBON ANALYSIS BASED ON LOW RESOLUTION RAMAN SPECTRAL ANALYSIS

[75] Inventor: Richard H. Clarke, Scituate, Mass.

[73] Assignee: Boston Advanced Technologies, Inc., Boston, Mass.

[21] Appl. No.: 583,808

[22] Filed: Sep. 17, 1990

[51] Int. Cl.⁵ .................. G01J 3/44; G01N 21/65
[52] U.S. Cl. ...................................................... 356/301
[58] Field of Search ............................................ 356/301

[56] References Cited

U.S. PATENT DOCUMENTS

| | | | |
|---|---|---|---|
| 2,527,121 | 10/1950 | Dudenhostel, Jr. | 356/301 |
| 3,697,180 | 10/1972 | Mori et al. | 356/301 |
| 3,817,634 | 6/1974 | Barron et al. | 356/301 |
| 3,850,525 | 11/1974 | Kaye | 356/73 |
| 3,914,055 | 10/1975 | Wolga et al. | 356/301 |
| 3,986,775 | 10/1976 | Chang et al. | 356/301 |
| 4,057,349 | 11/1977 | Barrett | 356/45 |
| 4,071,298 | 1/1978 | Falconer | 356/73 |
| 4,081,215 | 3/1978 | Penney et al. | 356/301 X |
| 4,505,586 | 3/1985 | Tochigi et al. | 356/301 |
| 4,620,284 | 10/1986 | Schnell et al. | 356/301 X |
| 4,624,561 | 11/1986 | Exton | 356/28.5 |
| 4,783,168 | 11/1988 | Florisson et al. | 356/301 |
| 4,802,761 | 2/1989 | Bowen et al. | 356/301 |
| 4,812,036 | 3/1989 | Inoue | 356/32 |
| 4,886,358 | 12/1989 | Pellenbarg et al. | 356/301 |

FOREIGN PATENT DOCUMENTS 1528418  10/1978  United Kingdom ............... 356/301

*Primary Examiner*—Vincent P. McGraw
*Attorney, Agent, or Firm*—Thomas J. Engellenner

[57] ABSTRACT

A system is disclosed for measuring properties of samples associated with the distribution of hydrocarbons in the sample. The system includes a low resolution laser Raman spectrometer coupled to photodetectors that integrate the intensity of the scattered Raman radiation. The system further includes microprocessor means that separate the Raman spectrum into two spectral ranges, calculates a ratio of the integrated intensities corresponding to these ranges and interpolates that ratio with a correlating function to obtain the measurement of the property of interest.

19 Claims, 5 Drawing Sheets

HYDROCARBON ANALYSIS BASED ON LOW RESOLUTION RAMAN SPECTRAL ANALYSIS

BACKGROUND OF THE INVENTION

The technical field of this invention is material analysis and, in particular, the invention relates to the determination of specific properties of hydrocarbon-containing fluids, such as the octane rating of gasolines.

Gasoline fuels are characterized by a series of physical properties, such as the octane number, the Reid Vapor Pressure (RVP), and the aromatic content. These fuels consist of a mixture of hundreds of hydrocarbon compounds, and the fuel properties are related to chemical grouping of these components. For example, the octane number of an unknown fuel may be related to the volume percent of monocyclic aromatics blended into the mixture. This particular property of gasolines, the octane number, plays a rather important role at the consumer level: car makers recommend gasolines of certain octane rating for their vehicles, and such ratings at the gas station pumps guide the choices of consumers.

Unfortunately, at present, there is no system to determine quickly and inexpensively the octane rating of gasolines or other gasoline properties, such as Reid vapor pressure and aromatic content.

In particular, the octane rating for finished gasolines is traditionally determined by an involved and expensive laboratory test in which the gasoline sample is run through a test engine under specified conditions referred to as "Research" (RON) and "Motor" (MON); the final octane assignment is reported to the consumer at the pump as (RON+MON)/2, the average of these two measurements. Despite the cumbersome and labor-intensive nature of this octane test, it remains the mainstay of octane verification for gasoline fuels both at the research and the consumer level.

Other fuel properties can be estimated by physical measurements, but ultimately these properties are, likewise, attributable to the chemical composition of the fuel.

Conventionally, one approach to determining the chemical composition of compounds, such as hydrocarbon fuels, has been to apply techniques, such as Infrared spectroscopy and Raman spectroscopy. These spectroscopic techniques can often characterize the majority of the organic compounds which make up a hydrocarbon fuel with some precision. Full chemical analysis of a fuel sample can lead to a complete characterization of all fuel properties, provided that all fuel components are accurately measured in their proper proportions. However, such a procedure is often very time-consuming and, in some instances, impossible by using a single analytical approach.

Raman spectroscopy provides direct information on the vibrational states of the molecules in the substance. These vibrational states, as revealed from the main features of the spectrum, provide the "signature" of the different molecules in a mixture; and the intensity of the "peaks" in the spectrum relates to the number of molecules in a particular vibrational state. From that information, the relative abundance of different molecular compounds in a mixture can be ascertained with high precision. See, for example, U.S. Pat. No. 2,527,121 which discloses the use of Raman scattering techniques to determine the aromatic content of hydrocarbon mixtures.

Conventional Raman spectroscopy usually required the use of large and complex instruments and required long exposure times in order to obtain a reliable spectrum. The introduction of lasers into Raman spectroscopy has lessened the problem of exposure times and has also provided enhanced spectral resolution. As such, laser Raman spectroscopy has been used for several years in analytical chemistry as a highly discriminating analytical tool, taking advantage of the high intensities delivered by laser sources. For this reason, it is also especially well-suited for microliter quantities of liquid samples. Moreover, high resolution Raman spectra can often be obtained in minutes over a wide frequency range to give quick and reliable identification of chemical components in a mixture, based on their vibrational spectral features. Nonetheless, such high resolution spectra still require the use of large and complex laser sources and spectrometers, making it almost impossible to adapt these techniques to field measurements of fuel properties.

There exists a need for low cost, portable fuel property measuring systems that do not depend on large and highly complex mechanical devices. Moreover, there exists the need of a system that exploits the chemical analysis of the fuel properties without the complexity and bulkiness of the usual spectroscopic systems.

SUMMARY OF THE INVENTION

The present invention discloses methods and systems for determining properties related to the hydrocarbon content of fluids, in particular, the octane rating of gasoline fuels. The system utilizes a laser Raman spectroscopic measurement of the hydrocarbon bands and relates specific band patterns to the fuel property of interest. Different fuel properties are determined by a method that compares Raman-scattered light intensities over different wavelength ranges.

In one aspect of this invention, systems are disclosed which correlate the laser Raman spectral features of a gasoline with the octane rating of that gasoline. The same approach may be used to measure RVP, aromatic content and other gasoline properties. Additionally, the invention consists of a Raman spectrometer configured specifically to recognize the spectral features that correlate with gasoline octane rating. The invention associates certain patterns in the Raman spectra of the fuel sample with the particular fuel property to be measured. These "patterns" in the Raman spectrum are also referred to herein as Raman bands. The same spectral pattern recognition approach of the invention can also be applied to the parametric determination of other gasoline and fuel properties, such as the Reid vapor pressure, the aromatic content, the distribution between monocyclic and bicyclic aromatic components and the level of additives. These properties are monitored by measuring the peak intensities and linewidths of at least two key Raman bands in the fuel spectrum.

This invention is particularly useful in that it can provide a quick and reliable determination of a number of fuel properties through a single spectral measurement on microliter fuel samples. The present invention thus permits octane ratings to be determined without resort to an elaborate, multi-step test engine procedure requiring about a liter of fuel.

The system monitors the integrated intensity (area under the peaks) of several spectral regions over the range of about 200 to 4000 wavenumbers (cm$^{-1}$). It is not necessary to fully resolve any bands in the chosen regions. The integrated intensities of selected bands lying before and after a selected wavelength are measured and ratios of these integrated intensities are calculated. The ratio of these areas can be compared with a correlating function in order to obtain the octane rating of the examined sample.

In one illustrated embodiment of the present invention, a low resolution, portable Raman spectrometer is disclosed. It can incorporate an immersible fiberoptic sensing probe, connected to a laser diode, as the source of scattering light, and a diode array for spectral pattern detection. The diode array output can be analyzed through an integrated microprocessor system configured to provide output in the form of specific fuel mixture properties. The use of optical fibers, laser diodes and diode arrays detectors allows that system to be small, portable and field-reliable. Another embodiment simply uses a laser light source in combination with appropriate cutoff filters and broadband photodetectors. This configuration can provide an inexpensive device that would permit the continuous testing of octane in a gas tank or fuel line.

The invention can also be used to monitor the properties of other hydrocarbon-containing fluids, such as lubricating oils and the like. Typically, lubricating oils will experience changes in their hydrocarbon composition over time, and such changes are indicative of loss of lubricating efficiency. The methods and apparatus of the present invention can be readily applied to monitor such changes.

The invention will next be described in connection with certain illustrated embodiments. Graphical data that show the various steps of the invention will also be presented. However, it should be clear that various changes, additions and subtractions can be made without departing from the spirit or the scope of the invention.

DETAILED DESCRIPTION

Figure 1:
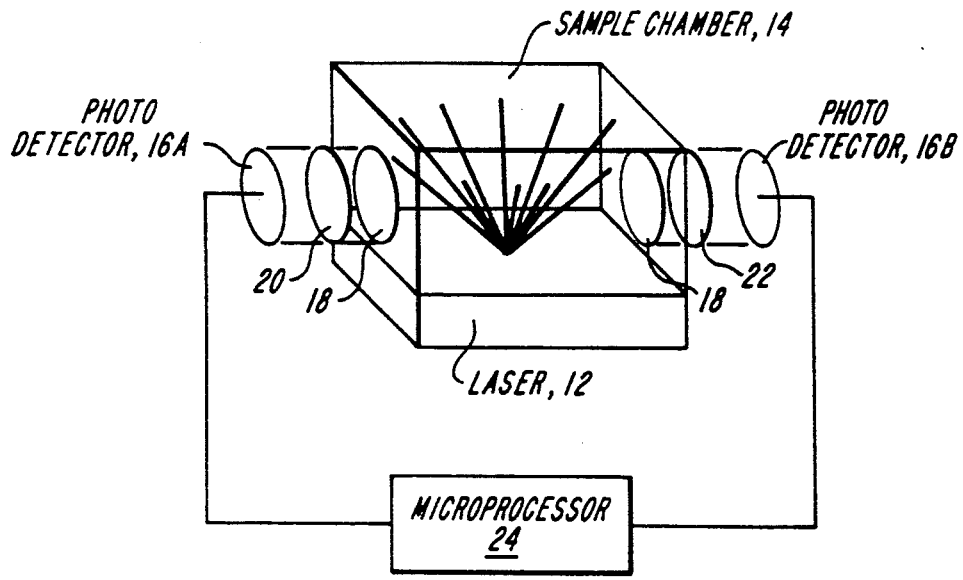
FIG. 1 is a block diagram of an on-line fluid-property monitor system according to the invention.

FIG. 1 is a block diagram of a sensor system 10 for measuring properties associated with the distribution of hydrocarbons in the fuel or other hydrocarbon-containing fluid. In this system, a laser source 12 (e.g., a continuous wave laser diode 12 operating at 805 nm with power ranging between 100-500 milliwatts) supplies coherent light into a sample chamber 14. Disposed adjacent to or within chamber 14 are two photodetectors 16A and 16B that detect the light scattered by the fuel sample. The photodetectors 16A and 16B can be constructed, for example, from simple photodiodes. Each photodetector is preceded by a set of filters 18 that reject light at the wavelength emitted by the laser source 12. Photodetector 16A is further filtered by low-pass filter 20 that transmits only a first range of the Raman spectrum (e.g., the light scattered in the region between 700 and 2000 wavenumbers), therefore, obtaining the integrated intensity of the scattered light in that spectral range. The other photodetector 16B is further filtered by high-pass filter 22 that transmits a second range of the Raman spectrum (e.g., the scattered light between 2000 and 4000 wavenumbers). The ratio output of the two detectors can then be calculated and compared with known data values in microprocessor 24 to quickly estimate the property of interest in the fuel sample. The system of FIG. 1 is well-suited for the on-line continuous monitoring of a fuel property, such as the octane rating.

It should be clear that other embodiments can be constructed employing more than two photodetectors. For example, rectangular chambers with four photodetectors, or other polygonal shapes having a photodetector incorporated into each wall, can be substituted for the sensor of FIG. 1.

Figure 2:
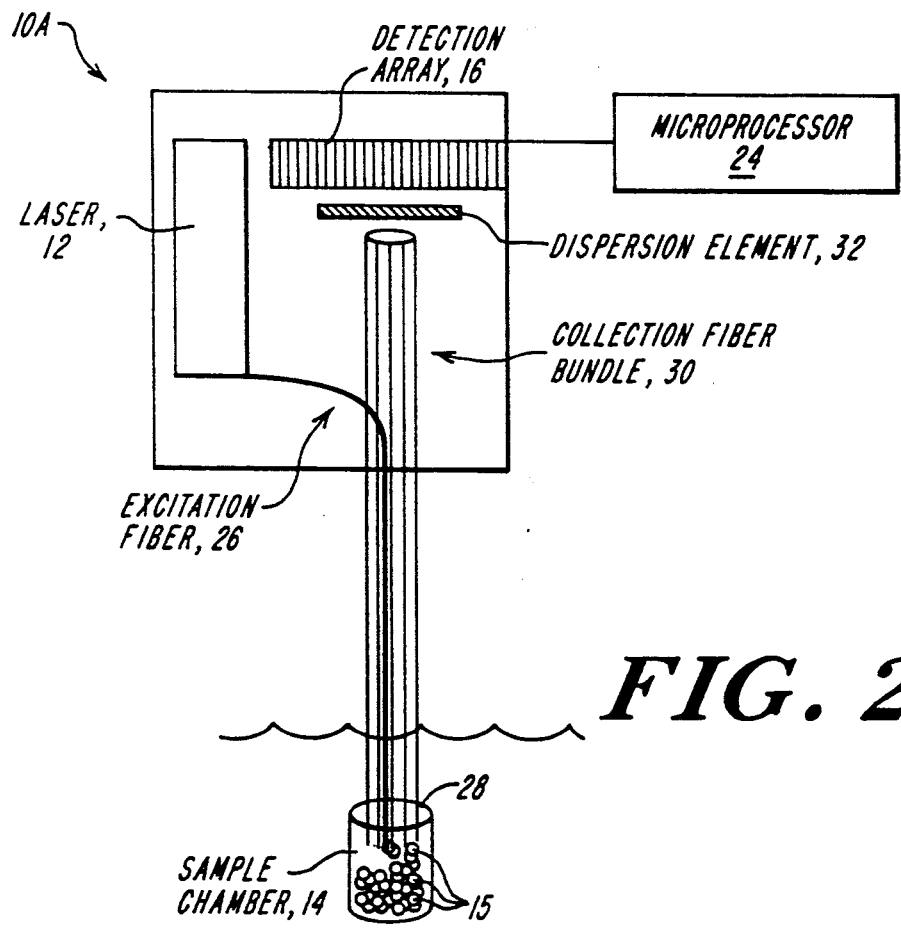
FIG. 2 is a block diagram of a portable fluid-property sensor system according to the invention.

FIG. 2 is a block diagram of another sensor system 10A that is particularly well-suited for sampling from a remote location and the measurement of several fuel properties at once. System 10A includes a laser source 12 connected to an excitation optical fiber 26 that carries the laser light to a sample chamber 14 that lies at a remote location. The sample chamber 14 can have at least one porous wall or surface 28. The sample chamber 14 can further include reflective elements 15 which enhance the collection of Raman scattered light from the sample. The Raman scattered light is collected by a flexible optical fiber bundle 30 that is also optically aligned with the sample chamber 14. The fiber bundle 30 can be coated to reject the wavelength of the laser source light. The Raman scattered light travels through the fiber bundle 30 into a dispersion device 32 that serves to disperse the scattered light into its different wavelength components. The dispersed scattered light is detected by photodetector array 16 that, in this case, consists of a photodiode array or a charged-coupled device (CCD) array.

Specific spectral bands of interest, such as the 1006 cm$^{-1}$ and 1450 cm$^{-1}$ bands for octane measurements (or others, for different fuel properties), are measured at low resolution to obtain the integrated band intensities. These bands can be narrow ones. For example, a first band centered around the 1006 cm$^{-1}$ peak can be chosen ranging from about 1004 to about 1008 cm$^{-1}$, and a second band from about 1445 to about 1455 cm$^{-1}$ can be chosen as the second range.

Again, with reference to FIG. 2, the resolving power of the dispersion device 32 determines the position of specific wavelengths in the diode array in such a way that the signal from a particular diode in the array will typically correspond to the same (or a similar) narrow range of wavelengths. This combination of the low-resolution dispersion device 32 and the diode array photodetector 16 thus form a Raman spectrometer. The microprocessor 24 selects a particular diode (or diodes) of the array 16 according to the fuel property to be measured. The integrated signals lying for the two ranges can be arithmetically divided to form intensity ratios. The microprocessor 24 compares these ratios with known values or a correlating function to obtain an estimate of the fuel property of interest.

Figure 3A:
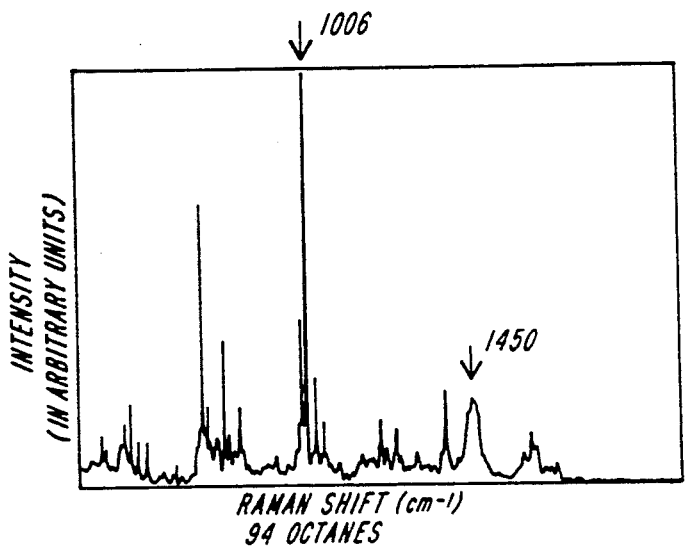
FIGS. 3A-3C are a series of graphs showing the variations in the Raman spectrum of fuel samples with different octane ratings.
Figure 3B:
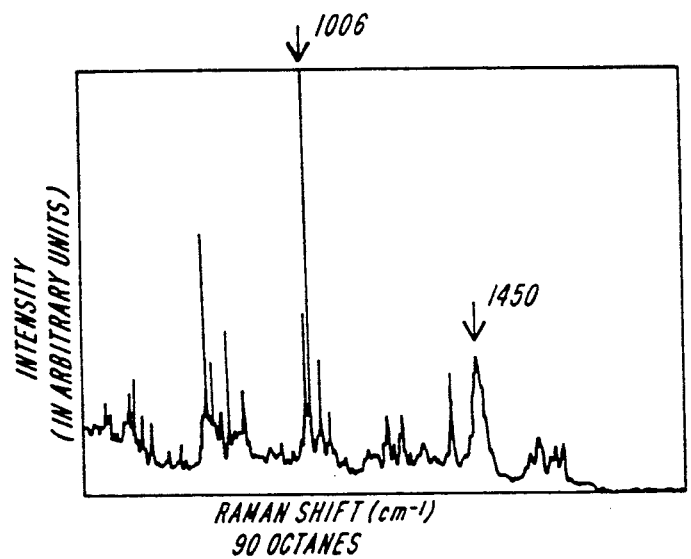
Figure 3C:
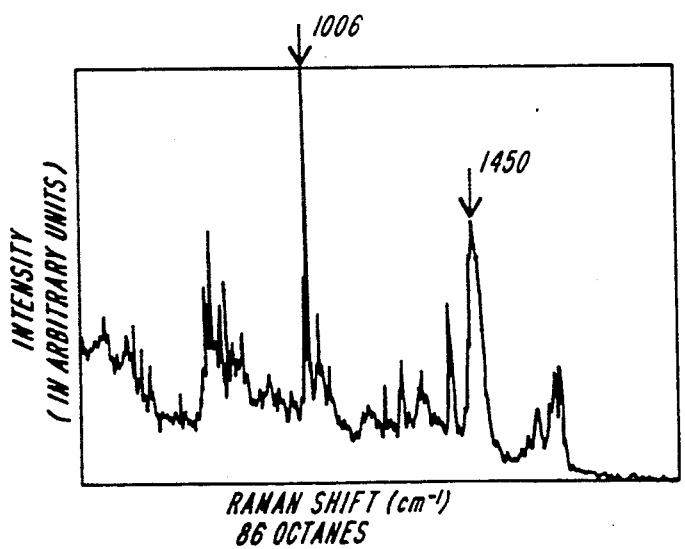

FIGS. 3A–3C are a series of Raman spectra as measured by the invention showing the overall pattern change for gasolines with different octane values. These figures show the variation of specific Raman bands (indicated by the arrows) for gasolines rated at 94, 90 and 86 octane, respectively. By displaying the Raman scattering profile for each gasoline sample over the range 400–2000 cm$^{-1}$, it becomes evident that the intensity of the 1450 cm$^{-1}$ band grows larger relative to the 1006 cm$^{-1}$ band as the octane rating decreases.

Figure 4:
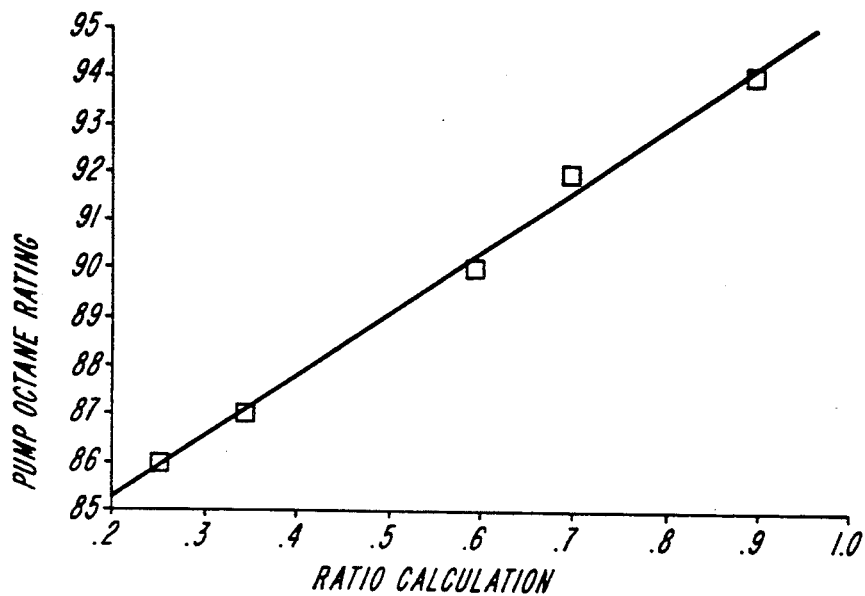
FIG. 4 is a graph that shows the correlation of integrated Raman scattering intensity for five samples of gasolines versus the pump octane rating of the gasoline sample.

This pattern of spectral changes is most readily appreciated when the ratio of the area under the peak at 1006 cm$^{-1}$ to that under the 1450 cm$^{-1}$ peak is plotted against pump octane rating. FIG. 4 is such a plot for a series of five commercial gasoline samples (of the same brand) whose octane value ranges between 86 and 94. The correlation coefficient of 0.993 (1.00 being a perfect correlation) shows the reliability of the method. A gasoline sample of unknown octane value can be readily evaluated by measuring its 1006/1450 intensity ratio and interpolating its octane value from the plot in FIG. 4.

It should also be noted that for at least some fluid properties an integrated area measurement may not be necessary. In such instances where sharp and distinctive peaks can be identified as strongly correlated with a certain property, the peak heights alone can be sufficient for ratio analysis.

Figure 5:
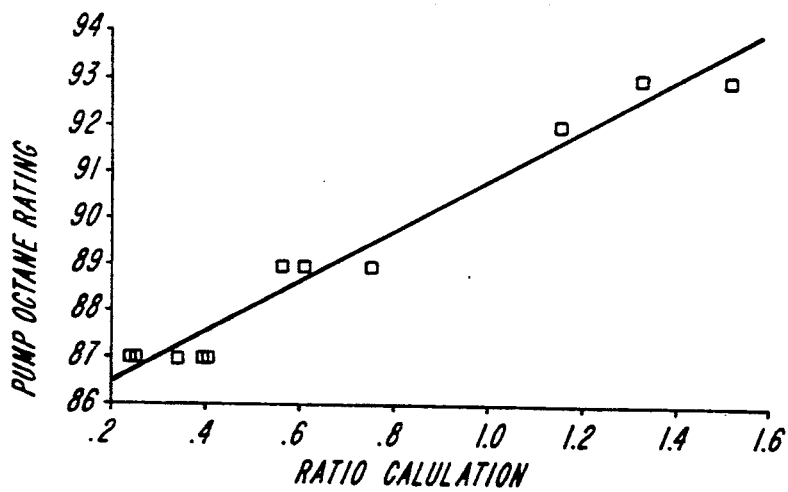
FIG. 5 is a graph showing the correlation for eleven brands of gasolines with different octane values.
Figure 6A:
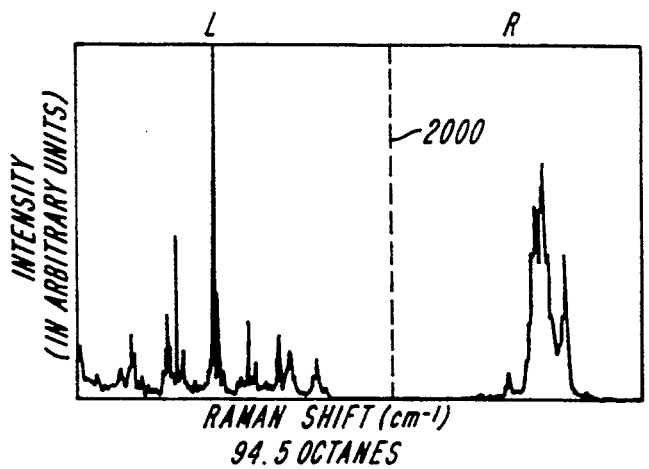
FIGS. 6A-6D are a series of graphs showing full range Raman spectra for gasolines of different octane values.
Figure 6B:
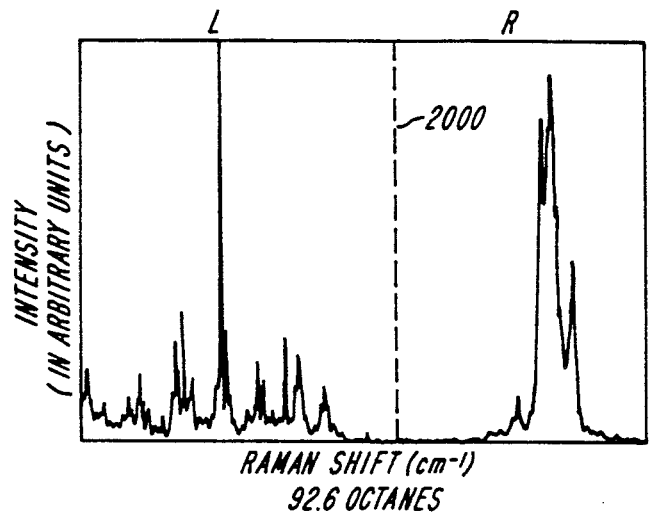
Figure 6C:
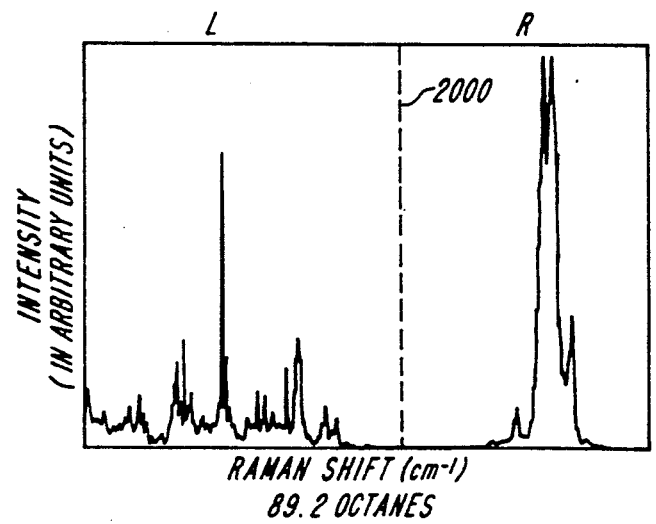
Figure 6D:
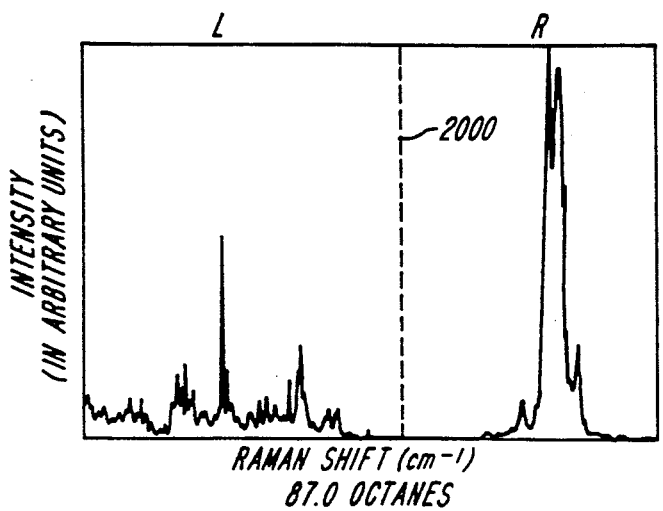

FIG. 5 is the same plot of 1006/1450 intensity ratio for eleven gasoline samples drawn from random commercial sources. The plot shows the same strong correlation between the 1006/1450 ratio and the pump octane rating (a correlation coefficient of 0.979), again allowing a determination of an unknown gasoline sample by measuring its 1006/1450 intensity ratio and interpolating its octane rating from the correlation established in FIG. 5. This shows that the method is independent of sampling gasolines from a single supplier.

FIGS. 6A–6D show the spectra of four typical gasoline samples of known octane rating ranging from 87.0 to 94.5 over the full spectral range between 200 and 3500 cm$^{-1}$. In this set of figures, the spectrum of each sample has been divided into ranges ("L" and "R"), representing scattered light either below or above about 2000 cm$^{-1}$, respectively.

Figure 7:
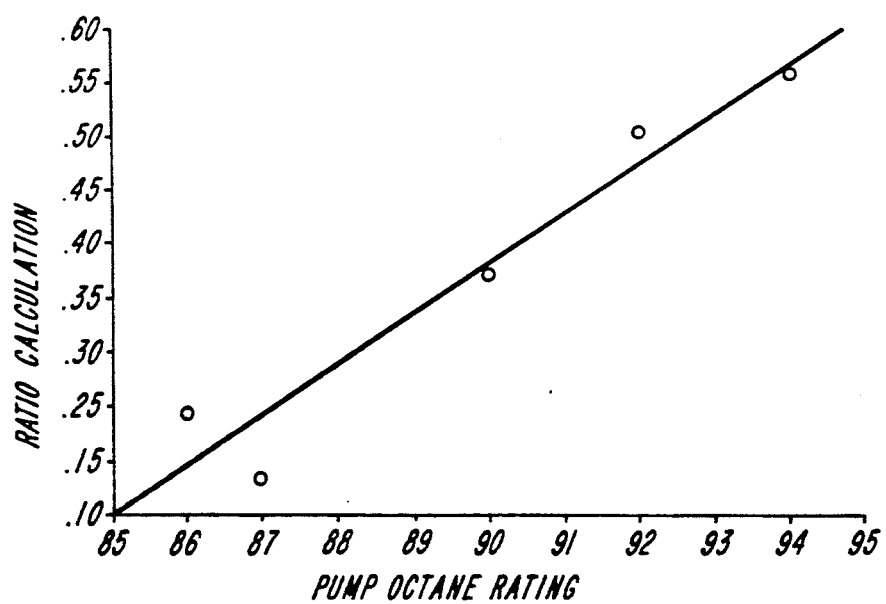
FIG. 7 is a graph showing the correlation for five brands of gasolines with different octane values.

FIG. 7 is a further correlation graph for five gasoline samples showing that the overall intensity of the spectral bands above 2000 cm$^{-1}$ increase systematically relative to the bands below 2000 cm$^{-1}$ as the gasoline octane rating decreases. This demonstrates that the method provided by the invention is broadly based on the Raman features of a gasoline sample and not narrowly dependent on the choice of a specific peak or band in the Raman spectrum.

What is claimed is:

1. A method for determining properties of a sample associated with the distribution of hydrocarbons in the sample comprising the steps of:
   irradiating a sample to produce a Raman spectrum of electromagnetic radiation which has been scattered as a result of irradiation;
   selecting at least a first range and a second, substantially non-overlapping, range in said spectrum, each of said ranges spanning more than one spectral peak;
   summing intensity values of said scattered radiation within each of said ranges; and
   comparing said values to provide a measurement of said properties of a sample.

2. The method of claim 1 wherein the method further comprises the step of acquiring said spectral ranges at a low resolution.

3. The method of claim 1 wherein the method further comprises the step of irradiating the sample with a continuous wave laser source to obtain said spectrum.

4. The method of claim 1 wherein the method further comprises the step of confining said spectrum to wavelengths between about 200 and about 4000 wavenumbers (cm$^{-1}$).

5. The method of claim 1 wherein the method further comprises the step of choosing a selected wavelength according to a particular property that is to be measured and then defining said first range to lie above said wavelength, and defining said second range to lie below said wavelength.

6. The method of claim 1 wherein the method further comprises the step of forming a ratio of said summed intensity values.

7. The method of claim 6 wherein the method further comprises the steps of comparing said ratio with a known value indicative of a sample property.

8. The method of claim 7 wherein the step of comparing values further comprises forming a linear correlating function from said ratios and said known values.

9. The method of claim 8, wherein the step of forming a correlation function further comprises the step of interpolating said ratio of said sample having an unknown value of said property with said linear correlating function.

10. An apparatus for measuring a property of a sample associated with the distribution of hydrocarbons in the sample, the apparatus comprising:
    means for irradiating a sample to produce a Raman spectrum of electromagnetic radiation which has been scattered as a result of irradiation;
    means for selecting at least a first range and a second, substantially non-overlapping, range in said spectrum, each of said ranges spanning more than one spectral peak;
    means for summing intensity values of said scattered radiation within each of said ranges; and
    means for applying said summed values to provide a measurement of the property of a sample.

11. The apparatus of claim 10 wherein said sample is irradiated by continuous wave laser means with power ranging between 100 and 500 milliwatts.

12. The apparatus of claim 10 wherein said spectral ranges are obtained by a photodetector.

13. The apparatus of claim 10 wherein the means for identifying said ranges further comprises at least two different filter elements.

14. The apparatus of claim 10 wherein the means for identifying said ranges further comprises a light dispersive element which cooperates with a spatial array of detector elements.

15. The apparatus of claim 10 wherein the apparatus further includes a sample chamber adapted to receive a sample.

16. The apparatus of claim 15 wherein the sample chamber further includes at least one porous wall.

17. The apparatus of claim 10 wherein the means for applying said summed values further comprises a microprocessor.

18. The apparatus of claim 10 wherein the means for applying said summed values further comprises means for defining a ratio of the summed values within one range to the summed values within another range.

19. The apparatus of claim 18 wherein the apparatus further comprises means for comparing said ratio with known values associated with a property to be measured.

* * * * *